(12) United States Patent
Horiguchi et al.

(10) Patent No.: US 9,616,154 B2
(45) Date of Patent: Apr. 11, 2017

(54) STIMULI-RESPONSIVE MATERIAL AND MEDICAL MATERIAL

(71) Applicant: Toray Industries, Inc., Tokyo (JP)

(72) Inventors: Tomoyuki Horiguchi, Otsu (JP); Kosaku Takeuchi, Otsu (JP); Yoshihiro Naruse, Nagoya (JP); Kazuhiro Tanahashi, Otsu (JP); Makito Yokoe, Nagoya (JP); Kohei Yamashita, Nagoya (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/377,051

(22) PCT Filed: Jan. 29, 2013

(86) PCT No.: PCT/JP2013/051813
§ 371 (c)(1),
(2) Date: Aug. 6, 2014

(87) PCT Pub. No.: WO2013/118605
PCT Pub. Date: Aug. 15, 2013

(65) Prior Publication Data
US 2015/0005409 A1    Jan. 1, 2015

(30) Foreign Application Priority Data

Feb. 8, 2012  (JP) .................. 2012-024673
Feb. 8, 2012  (JP) .................. 2012-024674
Jun. 28, 2012 (JP) .................. 2012-145164
Jul. 11, 2012 (JP) .................. 2012-155261
Jul. 11, 2012 (JP) .................. 2012-155262
Oct. 17, 2012 (JP) .................. 2012-229573

(51) Int. Cl.
| | | |
|---|---|---|
| A61L 31/04 | (2006.01) |
| A61L 24/04 | (2006.01) |
| A61L 15/22 | (2006.01) |
| A61L 15/42 | (2006.01) |
| A61L 24/00 | (2006.01) |
| A61L 26/00 | (2006.01) |
| C08K 7/00 | (2006.01) |
| C08L 33/26 | (2006.01) |
| C08J 5/04 | (2006.01) |
| C08K 3/08 | (2006.01) |
| D01D 5/36 | (2006.01) |
| D01F 6/90 | (2006.01) |
| D01F 6/92 | (2006.01) |
| D01F 8/12 | (2006.01) |
| D01F 8/14 | (2006.01) |

(52) U.S. Cl.
CPC .......... *A61L 31/041* (2013.01); *A61L 15/225* (2013.01); *A61L 15/42* (2013.01); *A61L 24/001* (2013.01); *A61L 24/0094* (2013.01); *A61L 24/043* (2013.01); *A61L 26/0095* (2013.01); *C08J 5/046* (2013.01); *C08K 7/00* (2013.01); *C08L 33/26* (2013.01); *A61L 2420/06* (2013.01); *C08J 2333/26* (2013.01); *C08J 2367/02* (2013.01); *C08J 2371/02* (2013.01); *C08K 2003/0812* (2013.01); *D01D 5/36* (2013.01); *D01F 6/90* (2013.01); *D01F 6/92* (2013.01); *D01F 8/12* (2013.01); *D01F 8/14* (2013.01)

(58) Field of Classification Search
USPC ................................. 523/105, 200; 524/916
See application file for complete search history.

(56) References Cited

U.S. PATENT DOCUMENTS

| | | | | |
|---|---|---|---|---|
| 5,393,379 A * | 2/1995 | Parrinello | ................. | C08J 5/06 162/101 |
| 6,117,949 A | 9/2000 | Rathi et al. | | |
| 8,683,798 B2 * | 4/2014 | Mather | ................ | B29C 70/882 427/113 |
| 2007/0196401 A1 * | 8/2007 | Naruse et al. | ................ | 424/401 |
| 2010/0137491 A1 | 6/2010 | Rose et al. | | |

FOREIGN PATENT DOCUMENTS

| | | |
|---|---|---|
| JP | 11-228850 | 8/1999 |
| JP | 2000-086729 | 3/2000 |
| JP | 2003-252936 | 9/2003 |
| JP | 2004-307523 | 11/2004 |
| JP | 2002-516910 | 2/2006 |
| JP | 2008-029226 | 2/2008 |
| JP | 2009-029967 | 2/2009 |
| JP | 2010-511751 | 4/2010 |
| JP | 2012-012606 | 1/2012 |

\* cited by examiner

*Primary Examiner* — Tae H Yoon
(74) *Attorney, Agent, or Firm* — DLA Piper LLP (US)

(57) ABSTRACT

A stimuli-responsive material includes a stimuli-responsive polymer, fibers and water, wherein the fibers have a number average diameter of 1 to 900 nm and are present in the stimuli-responsive material in a dispersed state; and a medical material and an anti-adhesive material, each of which includes a stimuli-responsive material including a stimuli-responsive polymer, fibers and water, wherein the fibers have a number average diameter of 1 to 900 nm and are present in the stimuli-responsive material in a dispersed state.

12 Claims, No Drawings

STIMULI-RESPONSIVE MATERIAL AND MEDICAL MATERIAL

CROSS-REFERENCE TO RELATED APPLICATIONS

This application is a 371 national stage application of PCT/JP2013/051813, filed on Jan. 29, 2013, which claims benefit to Japanese applications JP 2012-024673, filed on Feb. 8, 2012, JP 2012-024674, filed on Feb. 8, 2012, JP 2012-145164, filed on Jun. 28, 2012, JP 2012-155261, filed on Jul. 11, 2012, JP 2012-155262, filed on Jul. 11, 2012 and JP 2012-229573, filed on Oct. 17, 2012, which are hereby incorporated by reference in their entirety.

TECHNICAL FIELD

This disclosure relates to a stimuli-responsive material and a medical material comprising the same, the stimuli-responsive material specifically comprising a stimuli-responsive polymer, fibers and water.

BACKGROUND

A stimuli-responsive polymer of which volume or condition changes (it swells or shrinks) responding to a stimulus such as external heat, light, electric current, electric field and pH and which may be applicable to functional materials in various fields is generally known. For example, it has been suggested to be applied to drug carriers or anti-adhesive materials, medical materials for a drug delivery system, cosmetics, polymer actuator for driving moving parts of robots, chemical valve, material separator and optical elements. Particularly, the medical materials are regarded as the promising use of such materials.

Neighboring organs or organizations are adhered to each other when a wound such as inflammation, injury, excortication and operative wound heals. For example, an adhesion is caused after various surgeries accompanied with extirpation of diseased parts and restoration of damaged parts. A sheet type anti-adhesive material such as "SEPRAFILM" (made by Genzyme Biosurgery) and "INTERSEED" (made by Johnson & Johnson Company) is known as an adhesion barrier which works to prevent such an adhesion while a wound is healed in the body.

However, it is difficult for such an anti-adhesive material to be used for organs having a three-dimensional shape such as a cylinder shape or to medical equipment having a complex shape and are installed in the body. In addition, the above-described "SEPRAFILM" or the like may have poor handling ability when wet. Besides, it is too difficult for such a sheet type anti-adhesive material to be used in a recently increasing surgical operation using an endoscope or a laparoscope.

To improve the application convenience, a stimuli-responsive material supplied in a liquid state (or solid state) and produces an effect such as protection, separation, reinforcing and cushioning, in a solid state (or liquid state) brought about by a stimulus such as temperature change are known. JP 2003-252936-A discloses an application study of wound dressing material, surgical anti-adhesive material and adhesive with a material made of temperature-responsive polymer supplied as a liquid being fluid at room temperature into the body where it is solidified at body temperature and exhibits a barrier property after contacting the diseased parts in the operation using the endoscope or laparoscope.

A temperature-responsive polymer is one of such an attractive stimuli-responsive polymer. The temperature-responsive polymer generally includes two types of which a hydrated polymer is dehydrated to change the volume, formation or characteristics above the Lower Critical Solution Temperature (may be abbreviated as LCST) and of which a polymer is hydrated to change the volume, formation or characteristics below the Upper Critical Solution Temperature (may be abbreviated as UCST). The latter type of temperature-responsive polymer having the UCST may be a copolymer of N-acetyl acrylamide and acrylamide disclosed in JP 2000-86729-A. The former type of temperature-responsive polymer having the LCST may be a homopolymer or copolymer of N-isopropyl acrylamide (NIPAM) disclosed in JP 11-228850-A or may be a poloxamer. Particularly, a poly(N-isopropyl acrylamide) (PNIPAM)-based polymer compound is disclosed in JP 2004-307523-A. Such a compound changes volume as swelling-shrinking to form a solid gel around 32° C. close to body temperature and therefore it is expected to be applied to a medical material or the like.

Although such a stimuli-responsive polymer has an application convenience, it generally has too low an elasticity and strength to satisfy mechanical characteristics required for the use in a solid (gel) state. For example, it may have insufficient barrier characteristics for anti-adhesive materials. Further, it is well known that a transplanted artificial material different in mechanical characteristics from internal organs may cause a biological reaction according to the difference of the mechanical characteristics. Accordingly, a material having excellent mechanical characteristics like internal organs is needed. If the stimuli-responsive polymer is used to make an actuator, it should have a mechanical strength capable of sufficiently enduring drag applied to the actuator.

Accordingly, there are various new polymers improved in mechanical characteristics. For example, JP 2012-12606-A discloses temperature-responsive-gelating poly(ethylene glycol-block-(DL-lactic acid-random-glycolic acid)-block-ethylene glycol); (PEG-PLGA-PEG) triblock copolymer and (PLGA-PEG-PLGA) triblock copolymer. Further, JP 2009-29967-A discloses a branched block copolymer consisting of branched polyether and polyester.

However, even such a polymer material cannot make it possible that the stimuli-responsive function, mechanical characteristics and required characteristics such as biodegradability, biocompatibility and low toxicity are not achieved high dimensionally at the same time since introduced functional group to improve mechanical characteristics would relatively decrease the number of temperature-responsive groups.

Thus the application convenience and excellent mechanical characteristics have never been achieved with any stimuli-responsive material.

To achieve application convenience and high mechanical characteristics at the same time, it would be helpful provide for the improvement of mechanical characteristics of stimuli-responsive polymers. For example, workability and efficiency would be greatly improved if the strong coatability and convenience to carry and easily supply a material to an application site are achieved, when the material is used as general coating material such as paint, adhesive and sealant, or as medical coating material such as wound dressing material and anti-adhesive material. Specifically, it would be helpful if the material is supplied in a liquid state to firmly coat an application site by giving a stimulus. Particularly, conventional sheet-type anti-adhesive materials may have problems as to adhesiveness on complicated shapes, handling ability and supply characteristics to diseased parts in an endoscopic or laparoscopic surgery.

It would there be helpful to provide a stimuli-responsive material capable of achieving the application convenience and mechanical characteristics, as well as a medical material comprising the stimuli-responsive material.

SUMMARY

We thus provide a stimuli-responsive material containing a stimuli-responsive polymer, fibers having a number average diameter of 1 to 900 nm and water wherein the fibers are dispersed. We also provide a medical material comprising the stimuli-responsive material.

The stimuli-responsive material thus achieves application convenience and mechanical characteristics at the same time. Our materials also have another advantage of improving mechanical characteristics of various stimuli-responsive polymers.

DETAILED DESCRIPTION

The term "stimuli-responsiveness" means a tendency of changing in shape and/or characteristics as a result of responding to a stimulus such as illumination, electric field application, temperature (thermal) change, pH change and chemical addition. The tendency may be volume change such as swelling and shrinkage, sol-gel transition between liquid and solid states or formation change between liquid solution and liquid dispersion. Above all, our materials are advantageous in the sol-gel transition between liquid and solid states because the mechanical characteristics greatly change before and after responding to the stimulus. As to the stimuli-responsiveness, it is preferable that a difference of storage elastic moduli determined by a method described later before and after responding to the stimulus is more than or equal to 10 Pa, and is preferably more than or equal to 100 Pa, and further preferably more than or equal to 1,000 Pa.

Such a stimuli-responsive material may have an interaction between the stimuli-responsive polymer and fibers to improve stimuli-responsive polymer itself in mechanical characteristics such as strength, viscosity and shape stability. The stimuli-responsive material has a stimuli-responsiveness in concentration, proportion, chemical structure, shape or the like of the stimuli-responsive polymer or fibers. The stimuli-responsive polymer exhibits a stimuli-responsiveness under an appropriate condition such as concentration. The stimuli-responsive polymer changes before and after responding to a stimulus in shape and/or characteristics or the like and, therefore, may change in mechanical characteristics improvement with fibers. For example, a stimuli-responsive polymer having a low critical solution temperature (LCST) as to water could maintain a fluidity because of less mechanical characteristics improvement in a fluidity condition (sol) below the critical temperature while the polymer could improve the mechanical characteristics above the critical temperature uniquely. Also, the medical material such as anti-adhesive material in particular, which changes in shape and/or characteristics or the like before and after giving a stimulus could maintain a fluidity when supplied to diseased parts, while the medical material loses the fluidity after attaching to the diseased parts to function as an anti-adhesive material.

It is preferable that the storage elastic modulus is less than 100 Pa at 25° C. A storage elastic modulus less than 100 Pa can make a tube or spray-shaped equipment applicable to supply the material to a point of use and to discharge it from the point of use. It is more preferable that the storage elastic modulus is less than 50 Pa. To improve effects such as coating effect and anti-adhesion effect, it is preferable that a maximum storage elastic modulus is more than or equal to 100 Pa at 30 to 60° C., preferably at 30 to 45° C. It is preferable that the maximum storage elastic modulus is more than or equal to 300 Pa, and is preferably more than or equal to 1,000 Pa. The upper limit corresponding thereto is generally less than or equal to 50,000 Pa.

The maximum storage elastic modulus means the greatest storage elastic modulus in the range of measurement. The storage elastic modulus (G') is determined with a dynamic viscoelastic measuring equipment to which parallel plates are attached at intervals of 1 mm in the following condition after leaving a sample liquid for 5 min: 4 dyne/cm$^2$ of stress; 0.5° C./min of rate of temperature rise; 1 rad/s of angular velocity. The temperature-responsive polymer is measured at 25 to 60° C. The other materials are measured at 25° C. before giving a stimulus while measured at 30 to 60° C. after giving the stimulus.

A preferable stimuli-responsive polymer constituting the stimuli-responsive material may be poly(N-substituted acrylamide derivative) such as poly(N-isopropyl acrylamide), poly(N-isopropyl acrylamide-acrylic acid) copolymer, poly (N-isopropyl acrylamide-methyl methacrylate) copolymer, poly(N-isopropyl acrylamide-sodium acrylate) copolymer, poly(N-isopropyl acrylamide-vinyl ferrocene) copolymer and poly(vinyl methyl ether), poly(N-substituted methacrylamide derivative), hyaluronic acid derivative made by copolymerizing hyaluronic acid with a temperature-responsive polymer, polyamino acid derivative, polydepsipeptide, polyasparagine derivative synthesized from α/β-asparagine derivative, polypropylene oxide, copolymer of propylene oxide and another alkylene oxide, polyvinyl methyl ether, partial acetification product of polyvinyl alcohol, polyalkylene oxide, poly(ethylene glycol-block-(L-lactic acid)); (PEG-PLLA) diblock copolymer, poly(ethylene glycol-block-(D-lactic acid)); (PEG-PDLA) diblock copolymer, poly(ethylene glycol-block-(DL-lactic acid)); (PEG-PDLLA) diblock copolymer, (PEG-PLLA-PEG) triblock copolymer, (PEG-PDLA-PEG) triblock copolymer, (PEG-PDLLA-PEG) triblock copolymer, poly(ethylene glycol-block-DL-lactic acid-random-glycolic acid-block-ethylene glycol); (PEG-PLGA-PEG) triblock copolymer, (PLLA-PEG-PLLA) triblock copolymer, (PDLA-PEG-PDLA) triblock copolymer, (PDLLA-PEG-PDLLA) triblock copolymer, (PLGA-PEG-PLGA) triblock copolymer, (branched PEG-PLLA) block copolymer consisting of branched PEG and polylactic acid, (branched PEG-PDLA) block copolymer, (branched PEG-PDLLA) block copolymer, (branched PEG-PLGA) block copolymer, copolymer of lactide and polysaccharide, copolymer of polyether and polyester or its derivative, block copolymer of polyether copolymerized with polyester, hydroxy alkyl chitosan, copolymer of polyether side chain-introduced hydroxy acid unit and aspartic acid unit, or derivative or cross-linked polymer of them. An alkyl-substituted cellulose derivative such as methylcellulose, ethyl cellulose, hydroxypropyl cellulose, hydroxypropyl methylcellulose and hydroxyethyl methylcellulose, or a cellulose derivative made by copolymerizing cellulose with another temperature-responsive polymer may be employed if they have a high molecular weight or have a substituent introduced so as to exhibit the temperature responsivity. For example, although a simple carboxymethylcellulose may exhibit no temperature responsivity, a derivative of carboxymethylcellulose or methylcellulose copolymerized with polyalkylene oxide or the like is likely to exhibit the temperature responsivity as a desirable embodiment.

The stimuli-responsive polymer which responds to chemical addition may be an electrolyte or a combination of an ionic substance and strong ionic polymer. For example, cross-linked polymer of polyvinyl sulfonic acid or its derivative or the like can be combined with cationic surfactant. Alternatively, the sol-gel transition may be performed on cellulose acetate having a disulfide cross-link by the oxidation and reduction.

A humidity-responsive polymer may be cellulose acetate.

A photoresponsive polymer may be a polymer containing a compound such as diazo compound capable of performing cis-trans transition with light. It may also be a polymer of photoresponsive group-introduced carboxymethylcellulose capable of gelating with ultraviolet or a polymer of carboxymethylcellulose capable of gelating with radioactive ray.

A pH-responsive polymer may be an electrolyte-based polymer or a polymer having a basic group. Specifically, it may be cross-linked polyacrylic acid or its derivative or metal salt, polyacrylamide derivative, cross-linked polyalkyl sulfonic acid or its derivative or metal salt, cross-linked carboxy alkyl cellulose metal salt or the like.

It is possible that one or two kinds of stimuli-responsive polymers are contained. It is preferable to employ a stimuli-responsive polymer having a physical cross-link or the like to exhibit reversibility while a stimuli-responsive polymer capable of being cross-linked with chemical bond to exhibit irreversibility might cause a side reaction or unreacted residues.

It is preferable that the stimuli-responsive polymer is a temperature-responsive polymer suitable as medical materials. The temperature-responsive polymer may have 0 to 80° C. of UCST or LCST. It is preferable that the stimuli-responsive polymer is a temperature-responsive polymer having an LCST from a viewpoint of desirable use of the stimuli-responsive material. The Critical Solution Temperature may be a threshold temperature between different shapes and/or characteristics, a transition temperature between hydration and dehydration or the like. The temperature-responsive polymer having an LCST comes into a sol condition exhibiting a fluidity below the LCST while it comes into a gel condition exhibiting a solidity above the LCST. It is preferable that the critical solution temperature is 0 to 80° C. and preferably 20 to 70° C., from a viewpoint of easy handling at room temperature. The temperature-responsive polymer having a critical solution temperature of 20 to 50° C., suitable as medical materials responsive to body temperature as an external stimulus, easily develops an anti-adhesion effect. From a viewpoint of easy handling, it is preferable that the stimuli-responsive material having the anti-adhesion effect is biodegradable, and becomes liquid at room temperature while becoming solid gel in the body.

It is preferable that the critical solution temperature is adjusted depending on a practical use. For example, the critical solution temperature can be decreased by copolymerizing hydrophobic polymers or monomers and can be increased by copolymerizing hydrophilic polymers or monomers. The hydrophilic polymer compound may be polyethylene Oxide, polyvinyl alcohol or poly N-vinyl pyrrolidone. The critical temperature of a stimuli-responsive material is preferably adjusted appropriately because the critical temperature may be different from that of stimuli-responsive polymer which affects the critical temperature of the stimuli-responsive material.

It is preferable that the stimuli-responsive polymer contains a component having a number average molecular weight which is more than or equal to 3,000 and is preferably more than or equal to 10,000 to improve fibers in dispersibility.

It is preferable that the stimuli-responsive polymer is contained in the stimuli-responsive material by 50 wt % or less to achieve a marked change of shape and/or characteristics before and after stimuli-response. It is more preferable that the stimuli-responsive polymer is contained therein by 30 wt % or less, and preferably 20 wt % or less. It is preferable that the stimuli-responsive polymer is contained therein by 0.10 wt % or more to improve a stimuli-responsive material in mechanical characteristics. It is more preferable that it is contained therein by 0.50 wt % or more, preferably 1.0 wt % or more.

The stimuli-responsive material may be made from a natural fiber such as cellulose, chitin, chitosan, rayon and acetate, a regenerated fiber, a semisynthetic fiber or a synthetic fiber such as polyamide, polyester and polyolefin. From viewpoints of quality stability, fiber diameter uniformity, manufacturability of microfiber, strength and design flexibility, low cost, safety and the like, it is preferable that the stimuli-responsive material is made from synthetic fibers. For example, although cellulose fibers can be beaten to prepare cellulose nanofibers having microfibrils, such prepared cellulose nanofibers tend to fluctuate in fiber diameters to make quality unstable. The synthetic fibers may be made of polyester, polyamide, polyolefin, polyphenylene sulfide, phenolic resin, polyacrylonitrile, polyvinyl alcohol, polysulfone, fluorine-based polymer or derivatives of them.

The polyester may be polyethylene terephthalate, polytrimethylene terephthalate, polybutylene terephthalate, polylactic acid, polyglycolic acid or copolymer of them. The polyamide may be nylon 4, nylon 6, nylon 66, nylon 11 or copolymer of them. The polyolefin may be polyethylene, polypropylene, polystyrene or copolymer of them. It is possible that the fibers contain a combination agent such as fine particles, fire retardant and antistatic agent.

It is preferable that the stimuli-responsive material is made from fibers having an official moisture regain of 0.5 or more according to JIS L 1030-2 (2005) from a viewpoint of good fiber dispersibility. As preferable examples, nylon has official moisture regain of 4.5 while acrylic has that of 2.0 and polylactic acid has that of 0.5. On the contrary, polypropylene and carbon fibers have official moisture regain of 0.0 which might cause a bad dispersibility. It is preferable that the fiber official moisture regain less than 0.5 is reformed with fiber surface oxidation, grafting, or copolymerization or blending with hydrophilic component. Of course, it is preferable that even fiber official moisture regain more than or equal to 0.5 is reformed to improve dispersibility.

The stimuli-responsive material may contain fibers having a number average monofilament diameter of 1 to 900 nm. It is preferable that the number average diameter is less than or equal to 700 nm. It is preferable that it is less than or equal to 500 nm, preferably less than or equal to 200 nm. The number average diameter below 900 nm would improve fibers in dispersibility and mechanical characteristics with a notable interaction between fibers and the stimuli-responsive polymer. For example, fibers available for general clothes having fineness of 0.5 to 5 dtex (nylon 6 having density of 1.14 would have diameter of 7.5 to 23.6 μm) would tend to decrease in mechanical characteristics. On the other hand, the number average diameter above 1 nm would achieve an excellent handling and improve in mechanical characteristics.

From a viewpoint of excellent fiber dispersibility, it is preferable that the fibers have a length of less than or equal to 10.0 mm, preferably less than or equal to 5.0 mm. From viewpoints of handling ability and improvement of the stimuli-responsive material in mechanical characteristics, it is preferable that the fibers have a length of more than or equal to 0.01 mm, preferably more than or equal to 0.1 mm. From a viewpoint of excellent improvement of mechanical characteristics, it is preferable a ratio (L/D) of length to diameter is more than or equal to 200, and is preferably more than or equal to 1,000. From a viewpoint of excellent dispersibility, it is preferable that the L/D is less than or equal to 100,000, preferably less than or equal to 10,000.

The number average monofilament diameter and the fiber length are determined by the following methods. Samples are dried at 60° C. and then observed with a scanning electron microscope (SEM) or an optical microscope to measure monofilament diameters and fiber lengths of randomly selected 30 samples. This set of sampling and observation is repeated by 10 times to simply average the monofilament diameters and fiber lengths of total 300 samples. The fiber length above 5.0 mm is determined according to JIS L 1015 (2010) 8.4.1C method.

The synthetic fiber may be manufactured by a composite spinning method such as sea-island, blend and alloy types as well as a direct spinning method. The spinning method may be solution spinning, melt spinning, electrostatic spinning or the like. Above all, the sea-island type composite spinning method is preferable from viewpoint of low cost and uniformity of diameter.

The cellulose fiber may be derived from a plant such as wood, cotton, bamboo, hemp, jute, kenaf, farm waste, an animal such as ascidian, alga, microbe such as acetic acid bacteria (acetobacter). From a viewpoint of availability, the cellulose fiber is preferably derived from a plant. The cellulose fiber can be made by a conventional miniaturization method such as a fibrillation method or miniaturization method for attrition or beating with refiner, high-pressure homogenizer, medium agitating mil, stone mill, grinder or water jet, purification method with chemical treatment of acid hydrolysis, production method with microbe, fibrillation method in which fibers are disaggregated in wet conditions and then subjected to a steaming and physical treatment in the presence of an enzyme, electrostatic spinning method to make a regenerated cellulose fiber or a purified cellulosic fiber.

Chitin fiber can be extracted from living things or made with synthetic or semisynthetic polymer. The chitin fiber, which is included in a large amount in a crustacean shell of crabs or shrimps, has a monofilament diameter of 10-20 nm and a long fiber length of several mm, and is desirably employed with high mechanical characteristics. To extract the chitin fiber from crustacean shell, it is possible that the crustacean shell is milled to mix with alkali and then sufficiently stirred and washed and subsequently mixed with acid and then sufficiently stirred and washed. Alternatively, the crustacean shell may be ground with a grinder.

The fiber of stimuli-responsive material may be dispersed in water or stimuli-responsive polymer, or a composite body of water and stimuli-responsive polymer. In such a dispersion, the mechanical characteristics can be improved by an interaction with the stimuli-responsive polymer and the shape or characteristics can be changed before and after responding to the stimulus. Dispersion means a condition where fibers aren't constructed independently with interlacing or adhesion, as in nonwoven fabric, paper or sponges. With such a dispersion, the material consisting of stimuli-responsive polymer, fibers and water can exhibit a fluidity before or after a stimulus is given. From the viewpoint of dispersion stability and mechanical characteristics, it is preferable that monofilaments are mainly dispersed. It is possible that fiber bundles or fiber assemblies (less than 100 µm, for example) are dispersed or monofilaments are partially dispersed.

The dispersibility of fibers may be evaluated by a method in which randomly-selected parts of the stimuli-responsive material are observed with an optical microscope or a microscope to count the number of monofilaments with observed images divided into blocks so that the dispersibility is evaluated from unevenness of the number of fibers among the blocks.

It is preferable that a weight concentration of fiber is less than or equal to 10 wt % so that the shape and/or characteristics change notably before and after the response to the stimulus. It is preferably less than or equal to 5.0 wt %, preferably less than or equal to 3.0 wt %. To improve the stimuli-responsive material in mechanical characteristics, it is preferable that it is more than or equal to 0.01 wt %. It is preferably more than or equal to 0.10%, preferably more than or equal to 0.50 wt %.

It is preferable that the weight ratio (stimuli-responsive polymer/fiber) of a stimuli-responsive polymer to fibers is 5 to 100 in the stimuli-responsive material. A weight ratio below 100 can disperse fibers to the stimuli-responsive polymer appropriately to improve the mechanical characteristics. A weight ratio above 5 can notably improve fibers in mechanical characteristics. It is preferable that the weight ratio is 7 to 50, preferably 10 to 30. If the weight ratio is less than 1, the entanglement of fibers, less contribution of stimuli-responsive polymer or the like might prevent the material consisting of the stimuli-responsive polymer, fibers and water from exhibiting stimuli-responsivity.

To disperse the fibers, it is possible that fibers are stirred physically with a high-speed blender, a Henshel mixer, a super mixer, homogenizer or the like. Alternatively, another conventional method such as ultrasonic vibration dispersion method with an ultrasonic disperser may be employed. It is preferable that a surfactant is added to disperse the fibers desirably.

The stimuli-responsive polymer or fiber may have one or more basic chemical structures. The basic chemical structure means a unit constituting a polymer, such as lactic acid unit ($-O-CH(CH_3)-CO-$) in polylactic acid, propylene unit ($-CH_2-CH(CH_3)-$) in polypropylene, terephthalic acid and ethylene glycol unit ($-O-CO-C_6H_6-CO-O-CH_2CH_2-$) or glycol unit ($-CH_2CH_2-O-$) in polyethylene terephthalate, nylon 6 unit ($-CH_2CH_2CH_2CH_2CH_2-CO-NH-$) or amide unit ($-CO-NH-$) in nylon 6, glycol unit ($-CH_2CH_2-O-$) in polyethylene glycol, N-isopropyl acrylamide unit ($-CH_2CH(CO-NH-CH(CH_3)_2)-$) or amide unit ($-CO-NH-$) in poly(N-isopropyl acrylamide), glucose unit in cellulose, and glucosamine unit or amide unit ($-CO-NH-$) in chitin. It is preferable that the basic chemical structure is a unit constituting a main chain. Alternatively, it is possible that the unit is introduced in the main chain by a chemical modification or the like.

A solubility parameter (SP level) is a parameter specific to a material representing the solubility, hydrophilicity and hydrophobicity of the material. The SP level is determined by the Fedors' method [Fedors, R., PolymerEng. Sci., 14,147 (1974)]. In the Fedors' method, the SP level is calculated by Formula (1) on the basis that both cohesion energy density and molar volume depend on the kind and the number of substituents.

$$\delta = \sqrt{\frac{\sum E_{coh}}{\sum V}} \qquad (1)$$

($\Sigma E_{coh}$ is cohesion energy while $\Sigma V$ is molar volume.)

If the basic chemical structure consists of two or more kinds of segment, the SP level is calculated by summing solubility parameters of each basic chemical structure which have been multiplied by a ratio of the number average molecular weight of each basic chemical structure to the number average molecular weight of a whole molecule as shown in.

$$\delta = \sum_k \frac{Mn_k}{Mn} \cdot \delta_k \qquad (2)$$

($\delta$ is solubility parameter; $Mn_k$ is number average molecular weight of each basic chemical structure; Mn is number average molecular weight of a whole molecule; $\delta_k$ is solubility parameter of each basic chemical structure.)

If some kinds of basic chemical structure are contained, it is possible that at least one basic chemical structure is specified to calculate the SP level. Alternatively as shown in Formula (3), it is possible that the SP level of each basic chemical structure is multiplied by proportions of the number average molecular weight of each basic chemical structure and then summed to give an SP level of a stimuli-responsive material.

$$\delta = \sum_{k=1}^{N} \frac{Mn_k}{Mn} \cdot \delta_k \qquad (3)$$

($\delta$ is solubility parameter; $Mn_k$ is number average molecular weight of each basic chemical structure; Mn is number average molecular weight; $\delta_k$ is solubility parameter of each basic chemical structure.)

It is preferable that a difference between at least one kind of the SP level of the basic chemical structure in the stimuli-responsive polymer and the SP level of the basic chemical structure of the fibers is 0 to 10, so that the interaction is enhanced between the stimuli-responsive polymer and the fibers and the fibers are improved in dispersibility. It is preferable that the difference of the SP levels is 0 to 5, preferably 0 to 1.5. As to amide group (—NH—CO—), each of unit (—NH—) and unit (—CO—) gives a calculation result different from unit (—NH—CO—). In such a case, it is preferable that at least one calculation result is within the above-described range of the difference of SP levels. The calculation results of the SP levels are rounded off to one decimal place for the stimuli-responsive polymer and the fiber to obtain the difference therebetween as an absolute value.

It is preferable that the stimuli-responsive polymer has a basic chemical structure common to the fibers from a viewpoint of strong interaction with fibers. It is preferable that the basic chemical structure includes an amide unit, a hydroxy acid unit or a glucose unit in a part of the composition. Further, from a viewpoint of notable improvement of mechanical characteristics, it is preferable that the basic chemical structure includes an amide unit. Furthermore, from a viewpoint of biodegradability suitable for medical materials, it is preferable that the basic chemical structure includes an aliphatic hydroxycarboxylic acid unit. The aliphatic hydroxycarboxylic acid unit may be lactic acid unit (—O—CH(CH$_3$)—CO—), glycolic acid unit (—O—CH$_2$—CO—), glyceric acid unit (—O—CH$_2$—CH(OH)—CH$_2$—), hydroxybutyric acid unit (—O—CH(CH$_3$)—CH$_2$—CO—), malic acid unit (—O—CH(COOH)—CH$_2$—CO—) or the like. A plurality of these units can be mixed. If the composition has an asymmetric carbon atom, any kinds of optical isomers can be employed. Specifically, it is preferable to employ poly N-substituted acrylamide derivative, poly N-substituted methacrylamide derivative or particularly PNIPAM-based stimuli-responsive polymer in combination with chitin fiber or polyamide fiber such as nylon so that a common amide bond greatly improves the mechanical characteristics. The hydroxycarboxylic acid unit, specifically a stimuli-responsive polymer having a lactic acid unit in combination with fibers such as polylactic acid fiber and polyglycolic acid fiber could achieve both of biodegradability and excellent mechanical characteristics to be suitable for medical material such as anti-adhesion material. Even the chitin fibers have a biodegradability to be suitable for medical material. The polylactic acid can be made by a ring-opening polymerization of lactide which has been made by a dehydration condensation of two molecules of hydroxy carboxylic acid. The lactide may be L-lactide, D-lactide or DL racemic lactide, or may be copolymer, multi-block copolymer, graft copolymer of lactide with another monomer or the like.

The improvement of mechanical characteristics, of the stimuli-responsive polymer with fibers tends to increase greatly if the difference of SP levels between stimuli-responsive polymer and fibers is little, if the basic chemical structures are common, if the surface free energy is great or if the ratio (L/D) of fiber length to fiber diameter is great.

The stimuli-responsive material consists of a stimuli-responsive polymer, fibers and water. It is preferable that the stimuli-responsive polymer is dispersed and/or dissolved in water before or after responding to a stimulus.

It is preferable that a surfactant is contained to disperse or dissolve the stimuli-responsive polymer or fibers. The surfactant is preferably anionic or nonionic surfactant. A preservative, a dispersion stabilizer, an electrolyte or the like may be added if needed. The surfactant contained can improve mechanical characteristics. The greater molecular weight of the surfactant can improve the dispersibility by a steric repulsion between surfactants which have adhered to fibers. It is preferable that the surfactant has a number average molecular weight of 10,000 to 100,000, preferably 30,000 to 100,000. It is preferable that the surfactant is contained by 1 to 500 wt %, preferably 10 to 300 wt % relative to the fiber.

The stimuli-responsive material may be reversible or irreversible. Fibers contained can maintain the shape even if the stimuli-responsive material evaporates water.

The stimuli-responsive material has so high mechanical characteristics as to be suitable for a coating. The coating includes any of covering, adhering or sealing. The material for the coating may be coating material, sealing material, adhesion material, medical material or the like. Specifically, it is suitable for medical materials such as wound dressing material, anti-adhesion material, surgical adhesive and sealing material, for cosmetics such as foundation and hair conditioner and for industrial products such as adhesive, coating material and paint or the like. Above all, it is useful as a medical material since a liquid material can be supplied to diseased parts in a liquid state and changed by a stimulus to a solid material having high mechanical characteristics. The anti-adhesion material as a medical material is a preferable use from the viewpoint of application easiness to complex-shaped parts and application convenience effective for surgical operations such as laparotomy, laparoscope and endoscopic operation.

EXAMPLES

Physical properties in the Examples are measured by the following methods.
A. Polymer Melt Viscosity A polymer melt viscosity is measured with Capilograph 1B made by Toyo Seiki Seisaku-sho, Ltd. A polymer sample is injected and then retained for 10 min before starting the measurement.
B. Melting Point A melting point of the polymer is determined with Perkin Elmer DSC-7 by 2nd run as a peak-top temperature at which the polymer melts. The temperature is increased by 16° C./min with 10 mg sample.
C. Section Observation With a transmission electron microscope (TEM) (H-7100FA type made by Hitachi Corporation), a fiber is sliced along a cross section to make an ultrathin section to be observed. Nylon is subjected to a metal staining with phosphorus tungstic acid.
D. State Observation of Fiber Fiber dispersion liquid is sampled on a glass plate to be observed by 200 magnification with a microscope (Keyence Corporation).
E. Number Average Monofilament Diameter Samples are dried at 60° C. and then observed with an SEM to measure monofilament diameters to determine a simple average value. To collect samples of total 300 pieces to calculate a simple average value, 10 sets of diameter measurement are performed with respect to each set with 30 monofilaments randomly-selected from a 5 mm-square sample. To measure a diameter of a fiber having a modified cross section, a cross section area of a monofilament is measured at first, and the area is converted into a supposed area which the cross section would have if the cross section had a circular shape. The average monofilament diameter is calculated from the supposed area. Diameters of 300 monofilaments are measured with one decimal place in nm unit by observing photo images. Thus measured values are averaged and rounded off to a whole number.
F. Fiber Length Fiber length is determined according to JIS L 1015 (2010) 8.4.1C method. If thus determined fiber length is less than 5.0 mm, a fiber length calculated as follows is employed.

Samples are dried at 60° C. and then observed with an SEM or optical microscope to measure fiber lengths to determine a simple average value. To collect samples of total 300 pieces to calculate a simple average value, 10 sets of length measurement are performed with respect to each set with 30 monofilaments randomly-selected. Bent fibers are spread as possible to be measured appropriately. Fiber lengths of 300 monofilaments are measured with two decimal places in mm unit by observing photo images. Thus measured values are averaged and rounded off to one decimal place.

G. Storage Elastic Modulus (G')

A viscoelasticity is measured with a rheometer "Physica MCR301 (registered trademark)" made by Anton Paar. The measurement condition is as follows.
Plate: Parallel plate (φ25 mm)
Plate interval: 1 mm
Stress: 4 dyne/cm$^2$
Angular frequency: 1 rad/s
H. Dispersibility Evaluation of Fiber Fiber dispersion liquid is sampled on a glass plate to be observed by 200 magnification with a microscope (Keyence Corporation).
I. Calculation of SP Level A solubility parameter of the basic chemical structure is calculated with unit of $(J/cm^3)^{1/2}$ by Fedors' method and rounded off to one decimal place. A difference of SP levels is calculated from absolute values of SP levels of the stimuli-responsive polymer and the fiber.
J. Anti-adhesion Effect A rat is anesthetized with pentobarbital sodium and then cut to open the abdomen to expose the appendix. The appendix surface is wiped with Kimwipes and dried up. Then, a filter paper (1 cm×1 cm) including 40% ethanol solution is pasted on the exposed appendix and left for 5 min. After removing the filter paper, the serous membrane (5 mm×5 mm) is scratched in a part corresponding to the part which was pasted with the filter paper. The skin and muscular layer of the incision are sutured and then sterilized with a povidone-iodin. After two months from breeding, the rat is cut to open the abdomen and an adhesion has been found in a condition of the following score 3. Adhesion score based on macroscopic observation Score 0: No adhesion condition
Score 1: Weak adhesion condition to be released by picking the muscular layer up
Score 2: Middle adhesion condition to be released by tearing the muscular layer and the appendix off
Score 3: Strong adhesion condition to be hardly released even by tearing the muscular layer and the appendix off The anti-adhesion effect is evaluated by using the above-described model. 1 mL of the composition contained in a syringe of 2.5 mL is applied through a lancet of gauge 20 to the part which was pasted with the filter paper containing ethanol solution. At the time of the laparotomy after two months, any composition didn't have a macroscopic fraction in the abdominal cavity. The anti-adhesion effect is evaluated after two months.
Test 1

Example 1

50 wt % of Nylon 6 (N6; melting point 220° C.) having melt viscosity of 500 Pa·s (262° C.; shear speed 121.6 sec$^{-1}$) and 80 wt % of copolymerized polyethylene terephthalate (PET; melting point 225° C.) consisting of 8 mol % isophthalic acid (melting point 225° C.) having melt viscosity of 310 Pa·s (262° C.; shear speed 121.6 sec$^{-1}$) and 4 mol % bispenol A are blended at 260° C. with a biaxial kneading extruder to prepare polymer alloy chips having b* value of 4. The copolymerized PET has melt viscosity of 180 Pa·s at 262° C. and 121.6 sec$^{-1}$. Thus obtained polymer alloy melt is filtered and then melt-spun at 262° C. on a spinneret to make a composite fiber with 120 dtex-12 filaments. Thus obtained polymer alloy fiber is observed in the cross section with a TEM to find a sea-island component structure consisting of an island component (round regions) of N6 and sea component (other regions) of copolymerized PET.

Thus obtained composite fiber, from which the sea component has been removed with sodium hydroxide solution, is cut with a Guillotine cutter into fiber length of 1.00 mm. By observing the cross section of the fiber, we found that the number average monofilament diameter is 120 nm.

Next, the fiber and water are beaten in Niagara beater and further beaten with a PFI mill to prepare a mixture of 10 wt % fibers and water. 5.5 g of the mixture, nonionic surfactant (polyoxyethylene styrene sulfonated ether; number average molecular weight 10,000) and water are put in a disintegrator to disperse fibers in water.

Poly N-isopropyl acrylamide (PNIPAM; made by Aldrich Inc.; molecular weight 20,000-25,000) is added to thus obtained fiber dispersion to prepare a stimuli-responsive material. Thus obtained stimuli-responsive material has such characteristics as fiber weight concentration of 10 wt %, number average monofilament diameter of 120 nm, L/D of 8,333, surfactant weight concentration of 1.0 wt % and PNIPAM weight concentration of 10 wt %.

The stimuli-responsive material exhibits a fluidity at 25° C. and has storage elastic modulus of 20 Pa. It becomes a gel-like solid when heated to approximately 35° C. It also becomes a gel-like solid with no fluidity when it is dropped on the standard agar medium heated to 40° C. for observing the formation change. The storage elastic modulus at approximately 37° C. is 10,789 Pa, as maximum within 30-60° C. The result is shown in Table 1.

The SP level of N6 is 25.4 calculated based on unit (—$(CH_2)_6$—CONH—) while the SP level of PNIPAM is 24.6 calculated based on unit (—$CH_2$—CH—CONH—CH$(CH_3)_2$—). The difference of SP levels is 0.8.

Example 2

The test is performed by the same method of Example 1 except that the PNIPAM is replaced by a different amount of methylcellulose (MC: "METOLOSE SM4000" made by Shin-Etsu Chemical Co., Ltd.). Thus obtained stimuli-responsive material has such characteristics as fiber weight concentration of 1.0 wt %, number average monofilament diameter of 120 nm, L/D of 8,333, surfactant weight concentration of 10 wt % and MC weight concentration of 2.0 wt %. It is suspected that the fibers and stimuli-responsive polymer interacts less with the MC than with PNIPAM, for the mechanical characteristics improve less than Example 1. The stimuli-responsive material exhibits a fluidity at 25° C. and has storage elastic modulus of 57 Pa. It becomes a gel-like solid when heated to approximately 60° C., and the storage elastic modulus at approximately 60° C. is 920 Pa, as maximum within 30-60° C. The maximum storage elastic modulus within 30-45° C. is 157 Pa at approximately 45° C. It also becomes a gel-like solid with no fluidity when it is put on the standard agar medium heated to 70° C. for observing the formation change. The result is shown in Table 1.

The SP level of MC is 31.4 calculated based on unit (—CH—CH($OCH_3$)—CH(OH)—CH(O—)—CH($CH_2OH$)—O—) and, therefore, the difference of SP levels is 6.8.

Example 3

70 wt % of polylactic acid (PLA) and 30 wt % of copolymerized PET (random copolymer of ethylene glycol and dicarboxylic acid (terephthalic acid 61.25 mol %; isophthalic acid 26.25 mol %; 5-sulfoisophthalic acid monosodium (SSIA) 12.5 mol %)) are melt as each to be spun with a sea-island distribution spinneret, and then stretched by 4.4 times to prepare a sea-island composite fiber of 68 dtex-15 filaments.

Thus obtained sea-island composite fibers are bundled with a cloth inspection machine and cut with a Guillotine cutter into fiber length of 1.0 mm. Then, the sea component is subjected to a heat treatment for 5 min with water at 70° C. to be removed by dissolving. The composite fibers are washed to prepare a PLA fiber. By observing the cross section of the fiber, it is found that the number average monofilament diameter is 570 nm.

Next, the fiber and water are beaten in Niagara beater and further beaten with a PFI mill to collect fibers on the sieve to prepare a mixture of 8.4 wt % fibers and water. 23.8 g of the mixture, nonionic surfactant (polyoxyethylene styrenated phenyl ether) and water are put in a high-speed blender to disperse fibers in water at 13,900 rpm for 30 min.

The stimuli-responsive polymer (PLA-PEG-PLA) triblock copolymer (Mn 4, 420; PLA/PEG(w/w)=66/34), prepared based on a conventional method (Macromol. Res., 10, 6 (2002)), is added to thus obtained fiber dispersion to prepare a stimuli-responsive material. Thus obtained stimuli-responsive material has such characteristics as number average monofilament diameter of 570 nm, L/D of 1,754, fiber weight concentration of 0.9 wt %, stimuli-responsive polymer weight concentration of 15 wt %, ratio of stimuli-responsive polymer/fiber of 17 and surfactant weight concentration of 0.9 wt %.

The stimuli-responsive material exhibits a fluidity at 25° C. and has storage elastic modulus of 80 Pa. It becomes a gel-like solid when heated. The maximum storage elastic modulus within 30-60° C. is 380 Pa at approximately 33° C. The result is shown in Table 1.

The SP level of PLA is 22.8 calculated based on unit (—CH($CH_3$)—CO—O—). The SP level of the stimuli-responsive polymer is 21.6 calculated based on unit (—CH($CH_3$)—CO—O—; SP level 22.8) and unit (—$(CH_2)_2$—O—; SP level 19.2) with ratio of 66/34. Therefore the difference of SP levels is 1.2. On the other hand, the stimuli-responsive polymer has a basic chemical structure common to the fiber. Then, the SP level is would be 22.8 if calculated based on the main chemical structure (—CH($CH_3$)—CO—O—). Such a calculation would make the difference of SP levels zero.

Example 4

The test is performed by the same method of Example 3 except that the PLA fiber concentration is set to 0.6 wt %. Thus obtained composite material has such characteristics as number average monofilament diameter of 570 nm, L/D of 1,754, fiber weight concentration of 0.6 wt %, stimuli-responsive polymer weight concentration of 15 wt %, ratio of stimuli-responsive polymer/fiber of 25 and surfactant weight concentration of 0.9 wt %.

The stimuli-responsive material exhibits a fluidity at 25° C. and has storage elastic modulus of 17 Pa. The maximum storage elastic modulus within 30-45° C. is 135 Pa at approximately 35° C.

It is suspected that the fiber concentration of 0.9 wt % less than that of PLA fiber is not enough to sufficiently reinforce the stimuli-responsive polymer, for the maximum storage elastic modulus is less than that of Example 3.

Example 5

Like Example 3, 70 wt % of PLA and 30 wt % of copolymerized PET are melt as each. Next, they are spun with a sea-island distribution spinneret, and then stretched by 4.4 times to prepare a sea-island composite fiber of 45 dtex-10 filaments.

Thus obtained sea-island composite fibers are bundled with a cloth inspection machine and cut with a Guillotine cutter into fiber length of 1.5 mm. Then, the sea component is subjected to a heat treatment for 5 min with water at 70° C. to be removed by dissolving. The composite fibers are washed to prepare a polylactic acid fiber. By observing the cross section of the fiber, we found that the number average monofilament diameter is 810 nm.

Next, the fiber and water are beaten in Niagara beater and further beaten with a PFI mill to collect fibers on the sieve to prepare a mixture of fibers and water. The mixture, nonionic surfactant (polyoxyethylene styrenated phenyl ether; number average molecular weight 10,000) and water are put in a high-speed blender to disperse fibers in water at 13,900 rpm for 30 min.

The stimuli-responsive polymer (PLA-PEG-PLA) triblock copolymer is added to thus obtained fiber dispersion used in Example 3 to prepare a stimuli-responsive material. Thus obtained composite material has such characteristics as number average monofilament diameter of 810 nm, L/D of 1,852, fiber weight concentration of 0.9 wt %, stimuli-responsive polymer weight concentration of 15 wt %, ratio of stimuli-responsive polymer/fiber of 17 and surfactant weight concentration of 0.9 wt %.

The stimuli-responsive material exhibits a fluidity at 25° C. and has storage elastic modulus of 32 Pa. The maximum storage elastic modulus within 30-60° C. is 124 Pa at approximately 35° C.

It is suspected that the greater number average monofilament diameter increases the dispersibility, for the maximum storage elastic modulus is less than that of Example 3 even with the same fiber concentration as Example 3.

Example 6

The test is performed by the same method of Example 3 except that the stimuli-responsive polymer is replaced by poly(N-isopropyl acrylamide); (PNIPAM; made by Aldrich Inc.; molecular weight 20,000-25,000). Thus obtained composite material has such characteristics as number average monofilament diameter of 570 nm, L/D of 1,750, fiber weight concentration of 0.9 wt %, stimuli-responsive polymer weight concentration of 10 wt %, ratio of stimuli-responsive polymer/fiber of 11 and surfactant weight concentration of 0.9 wt %.

The stimuli-responsive material exhibits a fluidity at 25° C. and has storage elastic modulus of 70 Pa. It becomes a gel-like solid when heated. The maximum storage elastic modulus within 30-60° C. is 88 Pa at approximately 45° C. The maximum storage elastic modulus is lower than that of Example 3 in spite of improving to a higher value than that of PNIPAM itself after turning into gel.

The SP level of PLA is 22.8 calculated based on unit (—CH(CH$_3$)—CO—O—) while the SP level of PNIPAM is 24.6 calculated based on unit (—CH$_2$—CH—CONH—CH(CH$_3$)$_2$—). Therefore, the difference of SP levels is 0.8.

Comparative Example 1

The test is performed by the same method of Example 1 except that the fibers and nonionic surfactant are not added. The PNIPAM is added to water to prepare a polymer material. The PNIPAM weight concentration is 10 wt %. The stimuli-responsive material exhibits a fluidity at 25° C., and it becomes a gel-like solid when heated to approximately 35° C. However, the storage elastic modulus is small.

Comparative Example 2

The test is performed by the same method of Example 3 except that the fibers and nonionic surfactant are not added. The (PLA-PEG-PLA) triblock copolymer used in Example 3 is added to water to prepare a polymer material. The stimuli-responsive polymer weight concentration is 15 wt %. The polymer material exhibits a fluidity at 25° C., and it becomes a gel-like solid when heated. However, the maximum storage elastic modulus within 30-60° C. is only 47 Pa at approximately 34° C.

Comparative Example 3

The test is performed by the same method of Example 7 except that the fibers and nonionic surfactant are not added. The MC is added to water to prepare a polymer material. The MC weight concentration is 2.0 wt %. The stimuli-responsive material exhibits a fluidity at 25° C., and it becomes a gel-like solid when heated to approximately 60° C. However, the maximum storage elastic modulus is small.

Comparative Example 4

The test is performed by the same method of Example 1 except that the PNIPAM is not added. The fiber weight concentration is 10 wt %. The fiber dispersion material is not temperature-responsive and has inferior mechanical characteristics.

Comparative Example 5

The test is performed by the same method of Example 1 except that the fiber is replaced by N6 fibers of 22 dtex-20 filaments (single yarn fineness 1.1 dtex; diameter 11.1 μm) which have been cut into 1.00 mm. Thus obtained stimuli-responsive material has such characteristics as fiber weight concentration of 1.0 wt %, surfactant weight concentration of 1.0 wt % and PNIPAM weight concentration of 10 wt %. The stimuli-responsive material exhibits a fluidity at 25° C., and it becomes a slightly fluid gel when heated to approximately 35° C. However, the maximum storage elastic modulus is less than that of the PNIPAM itself with no reinforcement effect by the fiber.

Comparative Example 6

The test is performed by the same method of Comparative Example 4 except that the fiber concentration is replaced by 10 wt %. Thus obtained stimuli-responsive material has such characteristics as fiber weight concentration of 1.0 wt %, surfactant weight concentration of 1.0% and PNIPAM weight concentration of 10 wt %. The fiber is nondispersively-separated as exhibiting no temperature responsiveness. The storage elastic modulus cannot be measured.

Comparative Example 7

The test is performed by the same method of Example 3 except that the PLA fibers are replaced by 1.0 wt % of silica particles (diameter approximately 100 nm; "SNOWTEX MP1040" made by Nissan Chemical Industries, Ltd.). As a result, the maximum storage elastic modulus is found to be lower than that of the stimuli-responsive polymer itself.

Test 2

The anti-adhesion effects are evaluated with materials obtained in Examples 3 and 5 as well as Comparative Example 2. The result is shown in Table 2. According to the result, we found that our stimuli-responsive materials exhibit excellent anti-adhesion effect while a gel-like material made from stimuli-responsive polymer doesn't exhibit such an effect by itself.

TABLE 1

| | Fiber | | | | | Stimuli-responsive Polymer | | |
|---|---|---|---|---|---|---|---|---|
| | Materials | SP level | Diameter (nm) | Length (mm) | L/D | Concentration (wt %) | Polymer | SP level | Concentration (wt %) |
| Example 1 | N6 | 25.4 | 120 | 1.0 | 8 | 1.0 | PNIPAM | 24.6 | 10.0 |
| Example 2 | N6 | 25.4 | 120 | 1.0 | 8 | 1.0 | MC | 31.4 | 2.0 |
| Example 3 | PLA | 22.8 | 570 | 1.0 | 2 | 0.9 | PLA-PEG-PLA | 21.6 (22.8) | 15.0 |
| Example 4 | PLA | 22.8 | 570 | 1.0 | 2 | 0.6 | PLA-PEG-PLA | 21.6 (22.8) | 15.0 |
| Example 5 | PLA | 22.8 | 810 | 1.5 | 2 | 0.9 | PLA-PEG-PLA | 21.6 (22.8) | 15.0 |
| Example 6 | PLA | 22.8 | 570 | 1.0 | 2 | 0.9 | PNIPAM | 21.6 | 10.0 |
| Comparative Example 1 | — | — | — | — | — | — | NIPAM | 24.6 | 10.0 |
| Comparative Example 2 | — | — | — | — | — | — | PLA-PEG-PLA | 21.6 (22.8) | 15.0 |
| Comparative Example 3 | — | — | — | — | — | — | MC | 31.4 | 2.0 |
| Comparative Example 4 | N6 | 25.4 | 120 | 1.0 | 8 | 1.0 | — | — | — |
| Comparative Example 5 | N6 | 25.4 | 10000 | 1.0 | 0 | 1.0 | PNIPAM | 24.6 | 10.0 |
| Comparative Example 6 | N6 | 25.4 | 10000 | 1.0 | 0 | 10.0 | PNIPAM | 24.6 | 10.0 |
| Comparative Example 7 | Silica | 36.4 | Approx. 100 | Approx. 0.0001 | 1 | 1.0 | PLA-PEG-PLA | 21.6 (22.8) | 15.0 |

| | Weight ratio | SP level difference | Surfactant | Characteristics | |
|---|---|---|---|---|---|
| | Stimuli-responsive Polymer/Fiber | Polymer/Fiber | Concentration (wt %) | G' (Pa) 25° C. | G'MAX (Pa) 30-60° C. |
| Example 1 | 10 | 0.8 | 1.0 | 20 | 10789 |
| Example 2 | 2 | 6.0 | 1.0 | 57 | 2920 |
| Example 3 | 17 | 1.2 (0.0) | 0.9 | 80 | 380 |
| Example 4 | 25 | 1.2 (0.0) | 0.9 | 17 | 135 |
| Example 5 | 17 | 1.2 (0.0) | 0.9 | 32 | 124 |
| Example 6 | 11 | 1.2 | 0.9 | 70 | 88 |
| Comparative Example 1 | — | — | 0.0 | 4 | 11 |
| Comparative Example 2 | — | — | 0.0 | 0.001 | 47 |
| Comparative Example 3 | — | — | 0.0 | 28 | 231 |
| Comparative Example 4 | — | — | 1.0 | 20 | 20 |
| Comparative Example 5 | 10 | 0.8 | 1.0 | 8 | 10 |
| Comparative Example 6 | 1 | 0.8 | 1.0 | — | — |
| Comparative Example 7 | 15 | 14.8 (13.6) | 0.9 | 0.001 | 12 |

TABLE 2

| | Anti-adhesion effect |
|---|---|
| Example 3 | 0 |
| Example 5 | 1 |
| Comparative Example 2 | 3 |

INDUSTRIAL APPLICATIONS

Our stimuli-responsive materials are capable of achieving both application convenience and good mechanical characteristics and include medical materials comprising the stimuli-responsive material.

The invention claimed is:

1. A stimuli-responsive material comprising:
   a) 10 wt % to 50 wt % of a stimuli-responsive polymer,
   b) 0.5 wt % to 10 wt % of fibers, and
   c) water,
   wherein the fibers are dispersed in the stimuli-responsive polymer and water and have a number average diameter of 1 to 900 nm and the stimuli-responsive polymer and the fibers are selected from the following pairings of a polymer and a fiber:
   a) a polymer comprising a lactic acid unit (—O—CH(CH$_3$)—CO—) and a fiber comprising an ester unit (—CO—O—);
   b) a polymer comprising a terephthalic acid-ethylene glycol unit (—O—CO—C$_6$H$_6$—CO—O—CH$_2$CH$_2$—) and a fiber comprising an ester unit (—CO—O—);
   c) a polymer comprising a nylon 6 unit (—CH$_2$CH$_2$CH$_2$CH$_2$CH$_2$—CO—NH—) and a fiber comprising an amide unit (—CO—NH—) or a glucosamine unit; and
   d) a polymer comprising a glucosamine unit and a fiber comprising a glucosamine unit.

2. The stimuli-responsive material according to claim 1, wherein a weight ratio (stimuli-responsive polymer/fiber) of the stimuli-responsive polymer to the fiber is 5 to 100.

3. The stimuli-responsive material according to claim 1, wherein the stimuli-responsive polymer is a temperature-responsive polymer having a lower critical solution temperature.

4. The stimuli-responsive material according to claim 1, wherein a difference of Solubility Parameters of basic chemical structure of the stimuli-responsive polymer and the fiber is 0 to 5.

5. The stimuli-responsive material according to claim 1, wherein the stimuli-responsive polymer comprises a lactic acid unit and the fiber is a polylactic acid.

6. The stimuli-responsive material according to claim 1, wherein the fiber has a fiber length of 0.01 to 10.0 mm.

7. The stimuli-responsive material according to claim 1, wherein a ratio (L/D) of a fiber length to a fiber diameter is 200 to 100,000.

8. The stimuli-responsive material according to claim 1, further comprising a surfactant having a number average molecular weight of 10,000 to 100,000.

9. The stimuli-responsive material according to claim 1, wherein the stimuli-responsive material is a temperature responsive material having a low critical solution temperature.

10. The stimuli-responsive material according to claim 1, wherein a storage elastic modulus is less than 100 Pa at 25° C. and a maximum storage elastic modulus is 100 to 50,000 Pa within 30 to 60° C.

11. A medical material comprising the stimuli-responsive material according to claim 1.

12. An anti-adhesive material comprising the stimuli-responsive material according to claim 1.

* * * * *